US012681019B2

(12) United States Patent
Lauber et al.

(10) Patent No.: US 12,681,019 B2
(45) Date of Patent: Jul. 14, 2026

(54) HYDROPHOBICITY SHIFTED ENZYME

(71) Applicant: Waters Technologies Corporation, Milford, MA (US)

(72) Inventors: Matthew Lauber, North Smithfield, RI (US); Wenjing Li, Shrewsbury, MA (US)

(73) Assignee: Waters Technologies Corporation, Milford, MA (US)

( * ) Notice: Subject to any disclaimer, the term of this patent is extended or adjusted under 35 U.S.C. 154(b) by 588 days.

(21) Appl. No.: 18/167,152

(22) Filed: Feb. 10, 2023

(65) Prior Publication Data

US 2023/0258649 A1 Aug. 17, 2023

Related U.S. Application Data

(60) Provisional application No. 63/309,046, filed on Feb. 11, 2022.

(51) Int. Cl.
*G01N 33/68* (2006.01)

(52) U.S. Cl.
CPC ... *G01N 33/6821* (2013.01); *G01N 2333/976* (2013.01)

(58) Field of Classification Search
CPC ......... G01N 33/6821; G01N 2333/976; G01N 33/6818; C12Q 1/00
See application file for complete search history.

(56) References Cited

U.S. PATENT DOCUMENTS

2015/0361415 A1 12/2015 Meyer et al.

OTHER PUBLICATIONS

Chromatographyshop. Reverse phase liquid chromatography. https://chromatographyshop.com/knowledge/column-based-hplc-processes/reverse-phase-liquid-chromatography/. 2022; 1-5.*
Loziuk et al. Understanding the Role of Proteolytic Digestion on Discovery and Targeted Proteomic Measurements Using Liquid Chromatography Tandem Mass Spectrometry and Design of Experiments. J. Proteome Res. 2013;12:5820-5829.*
Egeland et al. The pros and cons of increased trypsin-to-protein ratio in targeted protein analysis. Journal of Pharmaceutical and Biomedical Analysis. 2016;123:155-161.*
Freije et al. "Chemically Modified, Immobilized Trypsin Reactor with Improved Digestion Efficiency." J. Prot. Res. 4 (2005): 1805-1813.
International Search Report and Written Opinion issued in International Application No. PCT/IB2023/051120 dated May 19, 2023.
Vankova et al. "Reversed-phase high-performance liquid chromatography of peptides of porcine pepsin prepared by the use of various forms of immobilzed a-chymotrypsin." J. Chromatogr. B. 753(2001): 37-43.

* cited by examiner

*Primary Examiner* — Lynn Y Fan
(74) *Attorney, Agent, or Firm* — WOMBLE BOND DICKINSON (US) LLP; Deborah M. Vernon; Ricardo Joseph

(57) ABSTRACT

The present invention relates to a method for analyzing a sample, the method comprising: (a) incubating a sample comprising an analyte with at least one enzyme to produce a digestion mixture comprising fragments of the analyte; (b) loading the digestion mixture onto a reversed-phase chromatography column; and (c) performing reversed-phase chromatography on the digestion mixture, wherein the at least one enzyme is hydrophobically modified to increase a retention time of the at least one enzyme such that the at least one enzyme elutes from the reversed-phase chromatography column later than the fragments of the analyte.

8 Claims, 2 Drawing Sheets

Specification includes a Sequence Listing.

HYDROPHOBICITY SHIFTED ENZYME

CROSS-REFERENCE TO RELATED APPLICATIONS

This patent application claims the priority and benefit of U.S. Provisional Application No. 63/309,046, filed Feb. 11, 2021, and entitled "HYDROPHOBICITY SHIFTED ENZYME", which is herein incorporated by reference in its entirety.

SEQUENCE LISTING

The instant application contains a ST.26 Sequence Listing which has been submitted electronically in XML format and is hereby incorporated by reference in its entirety. Said XML copy, created on Feb. 8, 2022, is named W-4415-US02.xml and is 11,297 bytes in size.

FIELD OF THE INVENTION

The present disclosure relates to a method for analyzing a sample using reversed-phase chromatography. In particular, the present disclosure relates to a method comprising the step of incubating the sample with a hydrophobically modified enzyme.

BACKGROUND OF THE INVENTION

Peptide mapping is an important characterization technique for elucidating the primary amino acid structure of proteins. In the biopharmaceutical industry in particular, peptide mapping is used for proof of identity, primary structural characterization and quality assurance/quality control (QA/QC) of recombinant protein pharmaceuticals, such as monoclonal antibodies (mAbs) and antibody-drug conjugates (ADCs).

Identifying a protein of interest using peptide mapping requires digestion of the protein by a protease enzyme, thereby producing a digestion mixture comprising peptide fragments of the protein. The digestion mixture is then separated by liquid chromatography, typically reversed-phase HPLC, to produce a chromatogram comprising a chromatographic peak for each of the peptide fragments present in the digestion mixture. This chromatogram is used to identify and/or structurally characterize the protein of interest.

One issue encountered during peptide mapping is that protease enzymes are themselves proteins. Accordingly, protease enzymes are capable of autolysis, i.e., self-digestion. As a result, digestion mixtures produced by mixing a protease enzyme with a protein of interest often contain enzyme fragments resulting from autolysis of the protease enzyme. Chromatographic peaks for these enzyme fragments appear in the chromatogram produced by the HPLC separation, contaminating the chromatogram and making identification and structural characterization of the protein of interest more difficult.

In an attempt to reduce the amount of enzyme autolysis that occurs during digestion of a protein of interest, the protease enzyme is typically mixed with the protein of interest in a low stoichiometric ratio (e.g. a 1:100 ratio of enzyme:protein of interest), i.e. the protein of interest is present in excess in the reaction mixture so that the probability of an enzyme molecule encountering a protein of interest molecule, and not another enzyme molecule, is increased. The issue with using a low stoichiometric ratio of enzyme is that not all of the molecules of the protein of interest will be digested during incubation with the enzyme. The resultant chromatographic peaks for the peptide fragments of the protein of interest are therefore of a low intensity, which also makes identification and structural characterization of the protein of interest more challenging.

One of the most common proteases used in peptide mapping is trypsin, a serine protease that cleaves peptide chains on the carboxyl side of the amino acids lysine and arginine. Trypsin is typically mixed with a protein of interest, during digestion, in a low stoichiometric ratio of between 1:100 to 1:20 (enzyme:protein).

More recently, proteases derivatized for resistance to autolysis have been developed. For example, trypsins alkylated on their lysine residues to prevent autolysis are commercially available. Such autolysis resistant proteases enable higher stoichiometric ratios of enzyme to be used in the protein digestion step of peptide mapping, resulting in more complete digestion of the protein of interest and more intense chromatographic peaks.

One issue that remains, in peptide mapping, is that often the intact protease enzyme is coeluted with the peptide fragments of the protein of interest. As a result, a peak for the intact enzyme appears in the chromatogram for the protein of interest. This intact enzyme peak can mask peaks, particularly less intense peaks, produced by peptide fragments of the protein of interest, thereby making identification and characterization of the protein of interest more challenging. The issue is exacerbated when using high stoichiometric ratios of autolysis resistant enzyme to protein of interest: the greater amount of enzyme present in the reaction mixture and the reduced amount of autolysis results in a more intense intact enzyme peak.

SUMMARY OF THE INVENTION

There exists the need for an improved method for peptide mapping, which addresses the issue of chromatogram contamination by intact enzyme peaks. The inventors of the present disclosure have developed one such method. The method of the present disclosure is not, however, limited to peptide mapping. Contamination of a chromatogram by an intact enzyme peak is also an issue in other analytical techniques involving cleavage of a molecule of interest by an enzyme, for example: DNA or RNA quantitation involving nuclease cleavage of the DNA or RNA of interest; and structural characterization of glycopeptides involving glycosidase digestion. The method of the present disclosure can be applied to such analytical techniques and enzymes other than proteases, to prevent intact enzyme peak chromatogram contamination.

According to the present invention there is provided a method for analyzing a sample, the method comprising:

- (a) incubating a sample comprising an analyte with at least one enzyme to produce a digestion mixture comprising fragments of the analyte;
- (b) loading the digestion mixture onto a reversed-phase chromatography column; and
- (c) performing reversed-phase chromatography on the digestion mixture, wherein the at least one enzyme is hydrophobically modified to increase a retention time of the at least one enzyme such that the at least one enzyme elutes from the reversed-phase chromatography column later than the fragments of the analyte. As the at least one enzyme elutes from the reversed-phase column later than the fragments of the analyte, intact enzyme peak chromatogram contamination is prevented.

Preferably, the at least one enzyme is selected from a protease, a nuclease, or a glycosidase. Exemplary proteases include: Lys-C; trypsin; chymotrypsin; Asp-N; Arg-C; Lys-N; and Glu-C. Exemplary nucleases include RNase H and RNase T1. An exemplary glycosidase is N-glycosidase.

Advantageously, the at least one enzyme is a protease.

Preferably, the protease is a hydrophobically modified trypsin.

Advantageously, the trypsin is a porcine trypsin (SEQ ID no. 1 is porcine trypsin). Porcine trypsin is more thermally stable than other forms of trypsin, such as bovine trypsin (SEQ ID no. 2 is bovine trypsin).

Preferably, the trypsin is resistant to autolysis. More preferably, the trypsin is derivatized by alkylation of lysine residues in the trypsin such that the trypsin is resistant to autolysis.

Advantageously, a stoichiometric ratio of the trypsin to the analyte in step (a) of the method (i.e., the incubation step) is from 1:20 to 2:1, and step (a) comprises incubating the sample with the trypsin: at a pH of from 5 to 9; at a temperature of from 20° C. to a melting temperature of the trypsin; and for a time period of less than or equal to 4 hours.

Preferably, the stoichiometric ratio of the trypsin to the analyte in step (a) of the method is 1:1. A stoichiometric ratio of between 1:20 and 2:1 aids in enabling tryptic digestion of the analyte to go to completion.

Advantageously, the protease is a cysteine protease, particularly hydrophobically modified IdeS (SEQ ID no. 3 is IdeS).

Preferably, the protease is resistant to autolysis. More preferably, the stoichiometric ratio of autolysis resistant protease to analyte in step (a) of the method is from 1:20 to 2:1. A stoichiometric ratio of from 1:20 to 2:1 aids in enabling digestion of the analyte to go to completion.

Advantageously, the or each enzyme is hydrophobically modified at the C-terminus.

Preferably, the or each enzyme is hydrophobically modified at the C-terminus with a sequence extension comprising at least three hydrophobic amino acid residues.

Advantageously, the or each enzyme is part of a fusion protein, wherein the or each fusion protein comprises a domain or a partial domain from a biologically derived protein domain, said domain or partial domain having a hydrophobicity index of greater than 25.

DETAILED DESCRIPTION OF THE INVENTION

The present invention provides a method for analyzing a sample. The method comprises: incubating a sample comprising an analyte with at least one enzyme to produce a digestion mixture comprising fragments of the analyte; and performing reversed-phase chromatography on the digestion mixture. In the method of the present invention, the at least one enzyme used to digest the analyte is hydrophobically modified to increase the retention time of the at least one enzyme such that the at least one enzyme elutes from the reversed-phase chromatography column later than all of the fragments of the at least one analyte.

The method of the present invention prevents the chromatogram for the analyte of interest being contaminated by an intact (non-degraded) enzyme peak.

While the method of the present invention relates to reversed-phase chromatography and concerns using one or more hydrophobically modified enzymes to carry out digestion of the analyte, when using other forms of chromatography, e.g., HILIC, it may, alternatively, be beneficial to hydrophilically modify the at least one enzyme, to increase its retention time.

Chromatogram Contamination by Intact Enzyme Peaks

Figure 1:
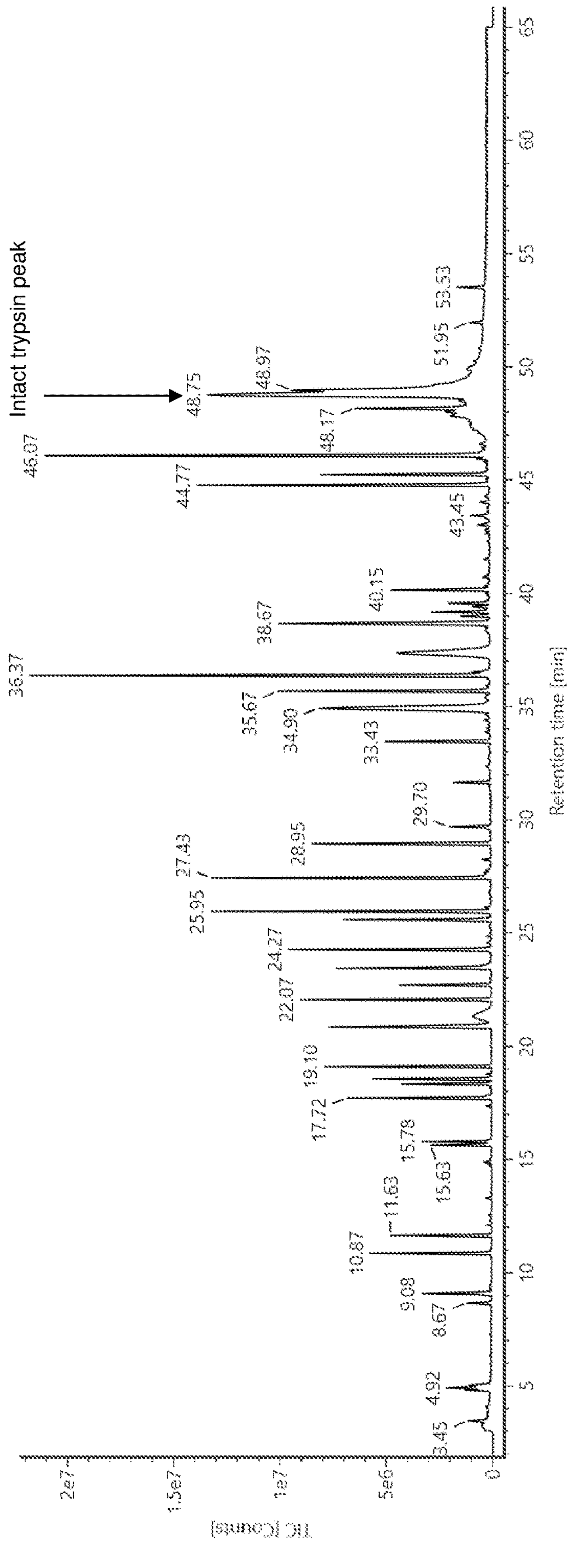
FIG. 1 shows a chromatogram obtained for the reversed-phase separation of a NIST® mAb digestion mixture, wherein the NIST mAb digestion mixture was produced by subjecting NIST mAb to a trypsin digest.
Figure 2:
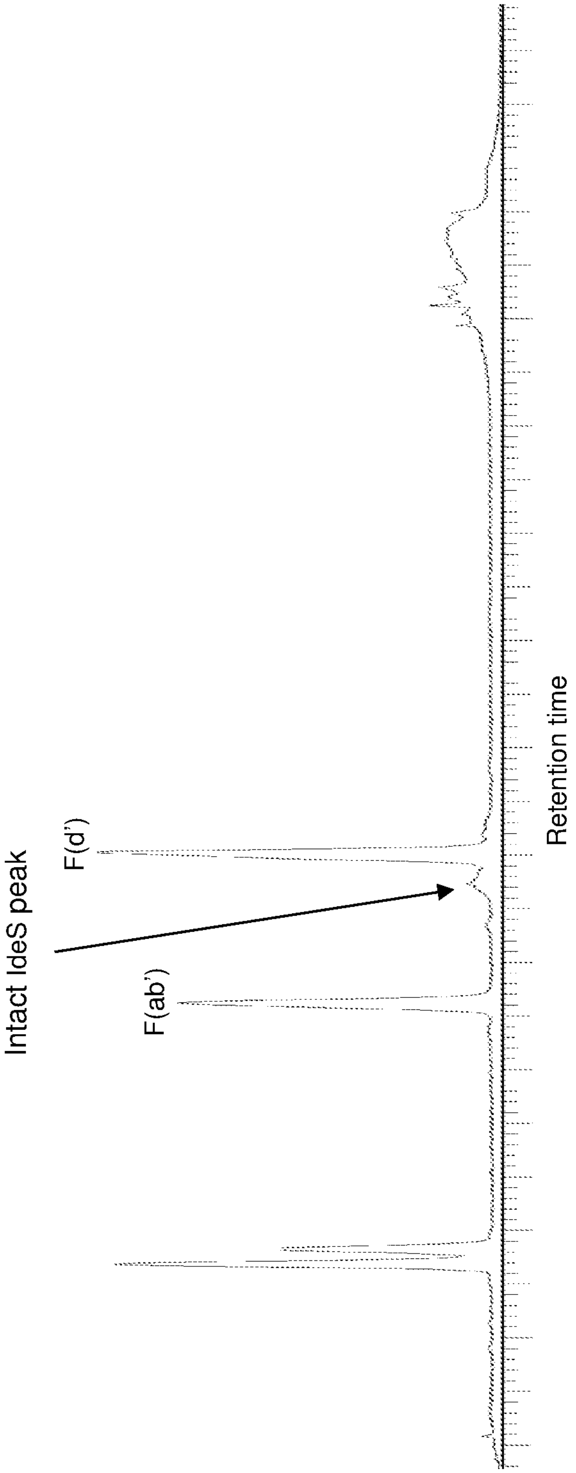
FIG. 2 shows a chromatogram obtained for the reversed-phase separation of an infliximab digestion mixture, wherein the infliximab digestion mixture was produced by subjecting infliximab to an IdeS protease digest.

FIGS. 1 and 2 highlight the issue of contamination of analyte chromatograms with intact enzyme peaks.

FIG. 1 shows a chromatogram obtained for the reversed-phase separation of a NIST mAb digestion mixture.

To produce the NIST mAb digestion mixture, NIST mAb, a humanised IgG1k monoclonal antibody, was denatured with GuHCl (guanidine chloride) and reduced with DTT (dithiothreitol) for 60 minutes at room temperature (20-25° C.), before being alkylated with iodoacetamide for 30 minutes at room temperature. The denatured NIST mAb protein was then desalted and subjected to trypsin (Marvelgent, Canton, MA, USA) digestion for 60 minutes at 37° C. The trypsin:NIST mAb molar ratio used in the digestion was 1:1. The digestion mixture was acidified with formic acid (FA) before being subjected to LC-MS analysis.

The reversed-phase chromatography column selected for carrying out the separation of FIG. 1 was an ACQUITY™ Premier Peptide CSH™ C18, 130 Å, 1.7 μm, 2.1×100 mm Column (Waters Corporation, Milford, MA, USA). The column was used with a flow rate of 0.25 ml/min. Mobile phase A used in the separation comprised 0.1% (v/v) FA in water and mobile phase B used in the separation comprised 0.1% (v/v) FA in acetonitrile. The column temperature was held at 65° C. during the separation.

The chromatographic peaks of FIG. 1 are labelled with accurate masses, obtained via online mass spectrometry.

The trypsin used to perform the tryptic digest of FIG. 1 had been derivatized, through extensive alkylation, e.g., dimethylation, of its lysine residues. Therefore, the trypsin used to perform the tryptic digest was highly autolysis resistant (resistant to self-digestion via peptide cleavage adjacent to lysine residues). Accordingly, the chromatogram of FIG. 1 is not contaminated by background chromatographic peaks produced by digested fragments of trypsin: the peaks in the chromatogram of FIG. 1 correspond almost exclusively to peptide fragments produced by the digestion of NIST mAb.

However, as can be seen in FIG. 1, intact trypsin present in the NIST mAb digestion mixture coeluted, at a retention time of between 47 to 50 minutes, with peptides fragments produced by the digestion of NIST mAb. The intact trypsin peak, in the chromatogram of FIG. 1, masks the peaks and their intensity for any peptide fragments of NIST mAb eluting at a similar retention time to the intact trypsin.

FIG. 2 shows a chromatogram obtained for the reversed-phase separation of an infliximab digestion mixture.

To produce the infliximab digestion mixture, infliximab (Remicade®), a chimeric monoclonal antibody used in the treatment of a number of autoimmune diseases, was diluted in 20 mM phosphate buffer (pH 7.1) to a concentration of 3 mg/ml and added to 100 units of IdeS protease (Promega, Madison, WI, USA). IdeS is an immunoglobulin degrading enzyme derived from *Streptococcus pyogenes*. The mixture was incubated for 30 min at 37° C. TCEP (tris(2-carboxyethyl)phosphine) and GuHCl were then added to denature and reduce the IdeS-digested infliximab and the digestion mixture was incubated for 1 hr at 37° C. prior to being subjected to chromatographic analysis.

The reversed-phase chromatography column selected for carrying out the separation of FIG. 2 was an ACQUITY UPLC™ BEH™, 300 Å, 1.7 μm, 2.1×150 mm Column (Waters Corporation, Milford, MA, USA). The column was used with a flow rate of 0.2 ml/min. Mobile phase A used in the separation comprised 0.1% (v/v) TFA (trifluoroacetic acid) in water and mobile phase B used in the separation comprised 0.1% (v/v) TFA in acetonitrile. The column temperature was held at 80° C. during the separation.

As can be seen in FIG. 2, intact IdeS protease present in the infliximab digestion mixture coeluted with fragments (F(ab') and Fd') of infliximab produced by digestion with IdeS protease.

The intact enzyme peak in FIG. 1 has an intensity (TIC count) comparable to that of the NIST mAb peptide fragments. This is not the case for the intact enzyme peak in FIG. 2. FIG. 1 highlights how the problem of chromatogram contamination with an intact enzyme peak is more acute when using autolysis resistant proteases in higher stoichiometric ratios.

While FIGS. 1 and 2 both relate to chromatograms obtained after protease digestion, FIGS. 1 and 2 are not limiting. Chromatogram contamination with an intact enzyme peak is also an issue for other enzymes, such as nucleases and glycosidases.

Method of Analyzing a Sample

The method for analyzing a sample of the present invention comprises: a step of digesting an analyte with at least one enzyme; and a step of carrying out reversed-phase chromatography on the resultant digestion mixture.

The digestion step may comprise incubating the analyte of interest with a single enzyme. Alternatively, the digestion step may comprise incubating the analyte of interest with multiple enzymes, either simultaneously or sequentially, e.g., the digestion step may comprise a multi-enzyme digestion. For example, the analyte of interest may be a protein and the protein may be subjected to a multi-enzyme digestion with both Lys-C and trypsin.

Where the digestion step comprises a multi-enzyme digestion, each of the enzymes used in the digestion may be hydrophobically modified, to prevent any of the intact enzymes eluting in the same retention time period as fragments of the analyte.

The conditions selected for carrying out the time digestion step, e.g., temperature, pH, and incubation time, will depend largely on the at least one enzyme. The temperature and pH may be selected to achieve optimal activity of the at least one enzyme.

In preferred aspects of the invention, the method comprises incubating the sample with the at least one enzyme at a temperature of from 20° C. up to a melting temperature of the at least one enzyme, or at a temperature of from 30° C. to 70° C.

For the majority of enzymes, the optimum pH for incubating the sample with the at least one enzyme will be a pH of 5 to 9.

In a preferred aspect of the invention wherein the at least one enzyme is a trypsin, the method comprises incubating the sample with the trypsin: at a temperature of from 20° C. up to a melting temperature of the trypsin, preferably at a temperature of from 30° C. to 70° C., more preferably at 37° C.; at a pH of 5 to 9, preferably at a pH of 6 to 8, more preferably at a pH of 6.5; and for a time period of less than or equal to 4 hrs, preferably less than or equal to 1 hr, more preferably less than 1 hr. A pH of 6.5 is advantageous for preventing pH induced modifications of the analyte during digestion. A relatively short incubation time can also help prevent additional modification of the analyte during digestion.

In aspects of the invention wherein the at least one enzyme is an enzyme resistant to autolysis, the preferred stoichiometric ratio of enzyme to analyte during incubation is from 1:20 to 2:1.

The sample comprising the analyte may be subjected to additional sample preparation steps, e.g., denaturation or reduction, prior to digestion.

Typically, the digestion mixture is loaded by injection onto the reversed-phase column through an injection valve. The digestion mixture may require clean-up, filtration, concentration, or other pre-analysis preparation prior to loading onto the reversed-phase column.

Reversed-phase chromatography columns suitable for performing the method according to the invention are known in the art and a suitable column can be selected for a given analyte of interest without undue experimentation.

The size of the column can be selected according to factors such as the amount of digestion mixture to be analysed. For example, for analysis of very small amounts of digestion mixture, a microbore column, a capillary column, or a nanocolumn may be used.

Once the digestion mixture has been successfully loaded onto the reversed-phase column, the digestion mixture is eluted from the column using a polar mobile phase. The mobile phase and elution gradient selected for performing the reversed-phase chromatography may be chosen to optimize the separation of the fragments of the analyte. Similarly, the column temperature used for the separation can be selected to optimize the separation of the fragments of the analyte. For example, the column temperature may be optimized to achieve the highest resolution separation.

A detector is used to detect components of the eluted sample and produce a chromatogram. In preferred aspects of the invention, the method comprises online mass spectrometry of the fragments of the analyte and the chromatogram is a mass chromatogram.

Hydrophobic Enzyme Modification

In the method of the present invention, one or more hydrophobically modified enzymes are used in the digestion step. Modification of an enzyme to increase its hydrophobicity causes the enzyme to have a greater affinity for the stationary phase of the reversed-phase chromatography column, thereby increasing the retention time of the enzyme on the column. It is possible, through hydrophobic modification, to increase the hydrophobicity of an enzyme sufficiently that intact enzyme in the digestion mixture does not elute during the same retention time period as fragments of the analyte, i.e., that an intact enzyme peak does not contaminate the chromatogram obtained for the digested analyte.

As used in the present disclosure, 'hydrophobically modified' means that the enzyme has been modified to comprise an additional hydrophobic component, thereby increasing the overall hydrophobicity of the enzyme.

Typically, enzymes used in analytical techniques are produced via recombinant engineering. A sample of recombinant enzyme contains fewer impurities than a sample of enzyme extracted from plant or animal sources.

Hydrophobic modification of an enzyme can also be achieved using recombinant engineering.

An enzyme of interest, e.g., a protease, nuclease or glycosidase, can be expressed, via recombinant engineering, modified with a C-terminal extension comprising hydrophobic amino acid residues (e.g., leucine, isoleucine, valine, phenylalanine, tryptophan, and methionine). Preferably, the enzyme can be expressed with a C-terminal extension comprising three or more hydrophobic amino acid residues.

The hydrophobic amino acid residues of the C-terminal extension may be spaced from the amino acid sequence of the enzyme (i.e., spaced by other non-hydrophobic amino acid residues), or may be interspersed with other non-hydrophobic amino acid residues. Spacing or interspersing the hydrophobic amino acid residues of the C-terminal extension may be advantageous for preserving the tertiary structure and activity of the enzyme. It is important that the hydrophobically modified enzyme is still capable of digesting the analyte of interest.

In preferred aspects, the enzyme of interest may be expressed with a C-terminal extension having a minimum GRAVY (grand average hydrophobicity index) of 2.5 and/or a hydrophobicity index greater than 25.

SEQ ID no. 4 is a representation of a recombinant porcine trypsin that comprises a C-terminal extension (SEQ ID no. 5) of repeating leucine and phenylalanine residues.

In an alternative aspect, an enzyme of interest, e.g., a protease, nuclease or glycosidase, can be expressed, via recombinant engineering, as part of a fusion protein, wherein the fusion protein also incorporates a domain or partial domain from a biologically derived protein domain, said domain or partial domain having a hydrophobicity index of greater than 25. For example, a fusion protein can be created that includes the enzyme of interest and a part of or a complete transmembrane domain.

SEQ ID no. 6 is a representation of a porcine trypsin-containing fusion protein. Said fusion protein also comprises transmembrane domain (SEQ ID no. 7) from *E. coli* outer membrane protein A.

In a further alternative aspect, an enzyme of interest can be modified, via recombinant engineering, to contain an amino acid residue that facilitates site specific conjugation with a hydrophobic moiety. For example, the enzyme can be recombinantly expressed with an additional C-terminal residue, such as a cysteine residue. The thiol group of the cysteine residue may then be derivatized with a hydrophobic moiety.

SEQ ID no. 8 is a representation of a porcine trypsin that comprises an additional C-terminal cysteine residue.

An example of a possible derivatization reaction for an enzyme modified to comprise an additional cysteine residue is a Michael addition reaction, e.g., a Michael addition with a hydrophobic maleimide containing moiety, such as the moiety depicted below.

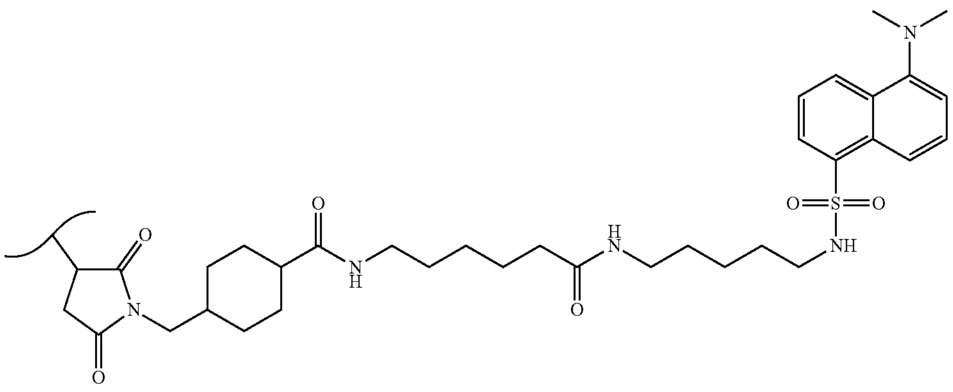

In the above structure, the wavy line indicates the point of attachment to the S atom of a cysteine residue.

It can be appreciated that introducing an amino acid residue that facilitates site specific conjugation with a hydrophobic moiety at the C-terminus is preferred over replacing an amino acid residue elsewhere in the enzyme with an amino acid residue that facilitates site specific conjugation with a hydrophobic moiety. Modification at the C-terminus is, generally, less likely to affect the tertiary structure and activity of the enzyme.

It can also be appreciated that, where the method involves multi-enzyme digestion, the different enzymes of the multi-enzyme digestion may comprise different hydrophobic modifications.

When used in the description and claims, the terms "comprises" and "comprising", and variations thereof, mean that the specified features, steps or integers are included. The terms are not to be interpreted to exclude the presence of other features, steps or components.

The invention may also broadly consist in the parts, elements, steps, examples and/or features referred to or indicated in the specification individually or collectively in any and all combinations of two or more said parts, elements, steps, examples and/or features. In particular, one or more features in any of the embodiments described herein may be combined with one or more features from any other embodiment(s) described herein.

Although certain example embodiments of the invention have been described herein, the scope of the appended claims is not intended to be limited solely to these embodiments. The claims are to be construed literally, purposively, and/or to encompass equivalents.

NUMBERED EMBODIMENTS

1. A method for analyzing a sample, the method comprising:
   (a) incubating a sample comprising an analyte with at least one enzyme to produce a digestion mixture comprising fragments of the analyte;
   (b) loading the digestion mixture onto a reversed-phase chromatography column; and (c) performing reversed-phase chromatography on the digestion mixture, wherein the at least one enzyme is hydrophobically modified to increase a retention time of the at least one enzyme such that the at least one enzyme elutes from the reversed-phase chromatography column later than the fragments of the analyte.

2. The method of embodiment 1, wherein the at least one enzyme is selected from a protease, a nuclease or a glycosidase.
3. The method of embodiment 2, wherein the at least one enzyme is a protease.
4. The method of embodiment 3, wherein the protease is a hydrophobically modified trypsin.
5. The method of embodiment 4, wherein the trypsin is a porcine trypsin.
6. The method of embodiment 4 or 5, wherein the trypsin is resistant to autolysis, preferably wherein the trypsin is derivatized by alkylation of lysine residues of the trypsin.
7. The method of embodiment 6, and wherein a stoichiometric ratio of the trypsin to the analyte in step (a) is from 1:20 to 2:1, and wherein step (a) comprises incubating the sample with the trypsin: at a pH of from 5 to 9; at a temperature of from 20° C. up to a melting temperature of the trypsin; and for a time period of less than or equal to 4 hours.
8. The method of embodiment 7, wherein the pH is from 6 to 8, preferably wherein the pH is 6.5.
9. The method of embodiment 7 or 8, wherein the temperature is from 30° C. to 70° C., preferably wherein the temperature is 37° C.
10. The method of any of embodiments 7 to 9, wherein the time period is less than or equal to 1 hour, preferably wherein the time period is less than 1 hour.
11. The method of any of embodiments 7 to 10, wherein the stoichiometric ratio of the trypsin to the analyte in step (a) is 1:1.
12. The method of embodiment 3, wherein the protease is a cysteine protease, preferably hydrophobically modified IdeS.
13. The method of embodiment 3, wherein the protease is resistant to autolysis, and preferably wherein a stoichiometric ratio of the protease to the analyte in step (a) is from 1:20 to 2:1.
14. The method of any preceding embodiment, wherein the or each enzyme is hydrophobically modified at the C-terminus.
15. The method of embodiment 14, wherein the or each enzyme is hydrophobically modified at the C-terminus with a sequence extension comprising at least three hydrophobic amino acid residues.
16. The method of any preceding embodiment, wherein the or each enzyme is part of a fusion protein, wherein the or each fusion protein further comprises a domain or partial domain from a biologically derived protein domain, said domain or partial domain having a hydrophobicity index greater than 25.

Amino Acid Sequences

The above description makes reference to the following proteins: porcine trypsin (SEQ ID no. 1); bovine trypsin (SEQ ID no. 2); IdeS (SEQ ID no. 3); a porcine trypsin comprising a C-terminal extension of repeating leucine and phenylalanine residues (SEQ ID no. 4); a porcine trypsin-containing fusion protein (SEQ ID no. 6); and a porcine trypsin comprising an additional C-terminal cysteine residue (SEQ ID no. 8). For completeness, the amino acid sequences for these proteins are provided below.

```
Porcine trypsin
IVGGYTCAANSIPYQVSLNSGSHFCGGSLINSQWVVSAAHCYKSRIQVRL

GEHNIDVLEGNEQFINAAKIITHPNFNGNTLDNDIMLIKLSSPATLNSRV

ATVSLPRSCAAAGTECLISGWGNTKSSGSSYPSLLQCLKAPVLSDSSCKS

SYPGQITGNMICVGFLEGGKDSCQGDSGGPVVCNGQLQGIVSWGYGCAQK

NKPGVYTKVCNYVNWIQQTIAAN

Bovine trypsin
IVGGYTCGANTVPYQVSLNSGYHFCGGSLINSQWVVSAAHCYKSGIQVRL

GEDNINVVEGNEQFISASKSIVHPSYNSNTLNNDIMLIKLKSAASLNSRV

ASISLPTSCASAGTQCLISGWGNTKSSGTSYPDVLKCLKAPILSDSSCKS

AYPGQITSNMFCAGYLEGGKDSCQGDSGGPVVCSGKLQGIVSWGSGCAQK

NKPGVYTKVCNYVSWIKQTIASN

IdeS
KRCYSTSAVVLAAVTLFALSVDRGVIADSFSANQEIRYSEVTPYHVTSVW

TKGVTPPAKFTQGEDVFHAPYVANQGWYDITKTFNGKDDLLCGAATAGNM

LHWWFDQNKEKIEAYLKKHPDKQKIMFGDQELLDVRKVINTKGDQTNSEL

FNYFRDKAFPGLSARRIGVMPDLVLDMFINGYYLNVYKTQTTDVNRTYQE

KDRRGGIFDAVFTRGDQSKLLTSRHDFKEKNLKEISDLIKKELTEGKALG

LSHTYANVRINHVINLWGADFDSNGNLKAIYVTDSDSNASIGMKKYFVGV

NSAGKVAISAKEIKEDNIGAQVLGLFTLSTGQDSW

Porcine trypsin having a C-terminal
extension of repeating Leu and Phe
residues
IVGGYTCAANSIPYQVSLNSGSHFCGGSLINSQWVVSAAHCYKSRIQVRL

GEHNIDVLEGNEQFINAAKIITHPNFNGNTLDNDIMLIKLSSPATLNSRV

ATVSLPRSCAAAGTECLISGWGNTKSSGSSYPSLLQCLKAPVLSDSSCKS

SYPGQITGNMICVGFLEGGKDSCQGDSGGPVVCNGQLQGIVSWGYGCAQK

NKPGVYTKVCNYVNWIQQTIAANLFLFLFLFLFLF

Porcine trypsin-containing fusion protein
IVGGYTCAANSIPYQVSLNSGSHFCGGSLINSQWVVSAAHCYKSRIQVRL

GEHNIDVLEGNEQFINAAKIITHPNFNGNTLDNDIMLIKLSSPATLNSRV

ATVSLPRSCAAAGTECLISGWGNTKSSGSSYPSLLQCLKAPVLSDSSCKS

SYPGQITGNMICVGFLEGGKDSCQGDSGGPVVCNGQLQGIVSWGYGCAQK

NKPGVYTKVCNYVNWIQQTIAANQLGAGAFGGYQVNPYVGFEMGYDWLGR

MPY

Porcine trypsin having an additional
C-terminal cysteine residue
IVGGYTCAANSIPYQVSLNSGSHFCGGSLINSQWVVSAAHCYKSRIQVRL

GEHNIDVLEGNEQFINAAKIITHPNFNGNTLDNDIMLIKLSSPATLNSRV

ATVSLPRSCAAAGTECLISGWGNTKSSGSSYPSLLQCLKAPVLSDSSCKS

SYPGQITGNMICVGFLEGGKDSCQGDSGGPVVCNGQLQGIVSWGYGCAQK

NKPGVYTKVCNYVNWIQQTIAANC
```

SEQUENCE LISTING FREE TEXT

Each of SEQ ID nos. 4 to 8 are synthetic sequences.

We claim:

1. A method for analyzing a sample, the method comprising:

(a) incubating a sample comprising an analyte with hydrophobically modified trypsin to produce a digestion mixture comprising fragments of the analyte;

(b) loading the digestion mixture onto a reversed-phase chromatography column; and (c) performing reversed-phase chromatography on the digestion mixture, wherein the hydrophobically modified trypsin is hydrophobically modified at the C-terminus with a sequence extension comprising at least three hydrophobic amino acid residues to increase a retention time of the hydrophobically modified trypsin such that the hydrophobically modified trypsin elutes from the reversed-phase chromatography column later than the fragments of the analyte.

2. The method of claim 1, wherein the hydrophobically modified trypsin is a hydrophobically modified porcine trypsin.

3. The method of claim 1, wherein the hydrophobically modified trypsin is resistant to autolysis.

4. The method of claim 1, wherein the hydrophobically modified trypsin is derivatized by alkylation of lysine residues of trypsin.

5. The method of claim 1, and wherein a stoichiometric ratio of the hydrophobically modified trypsin to the analyte in step (a) is from 1:20 to 2:1, and wherein step (a) comprises incubating the sample with the hydrophobically modified trypsin: at a pH of from 5 to 9; at a temperature of from 20° C. up to a melting temperature of the hydrophobically modified trypsin, and for a time period of less than or equal to 4 hours.

6. The method of claim 5, wherein the stoichiometric ratio of the hydrophobically modified trypsin to the analyte in step (a) is 1:1.

7. The method of claim 1, wherein a stoichiometric ratio of the hydrophobically modified trypsin to the analyte in step (a) is from 1:20 to 2:1.

8. The method of claim 1, wherein the hydrophobically modified trypsin is part of a fusion protein, wherein the fusion protein further comprises a domain or partial domain from a biologically derived protein domain, and wherein the domain or partial domain has a hydrophobicity index greater than 25.

* * * * *

SEQUENCE LISTING

```
Sequence total quantity: 8
SEQ ID NO: 1           moltype = AA  length = 223
FEATURE                Location/Qualifiers
source                 1..223
                       mol_type = protein
                       organism = Sus domesticus
SEQUENCE: 1
IVGGYTCAAN SIPYQVSLNS GSHFCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DSCQGDSGGP  180
VVCNGQLQGI VSWGYGCAQK NKPGVYTKVC NYVNWIQQTI AAN                    223

SEQ ID NO: 2           moltype = AA  length = 223
FEATURE                Location/Qualifiers
source                 1..223
                       mol_type = protein
                       organism = Bos taurus
SEQUENCE: 2
IVGGYTCGAN TVPYQVSLNS GYHFCGGSLI NSQWVVSAAH CYKSGIQVRL GEDNINVVEG  60
NEQFISASKS IVHPSYNSNT LNNDIMLIKL KSAASLNSRV ASISLPTSCA SAGTQCLISG  120
WGNTKSSGTS YPDVLKCLKA PILSDSSCKS AYPGQITSNM FCAGYLEGGK DSCQGDSGGP  180
VVCSGKLQGI VSWGSGCAQK NKPGVYTKVC NYVSWIKQTI ASN                    223

SEQ ID NO: 3           moltype = AA  length = 335
FEATURE                Location/Qualifiers
source                 1..335
                       mol_type = protein
                       organism = Streptococcus pyogenes
SEQUENCE: 3
KRCYSTSAVV LAAVTLFALS VDRGVIADSF SANQEIRYSE VTPYHVTSVW TKGVTPPAKF  60
TQGEDVFHAP YVANQGWYDI TKTFNGKDDL LCGAATAGNM LHWWFDQNKE KIEAYLKKHP  120
DKQKIMFGDQ ELLDVRKVIN TKGDQTNSEL FNYFRDKAFP GLSARRIGVM PDLVLDMFIN  180
GYYLNVYKTQ TTDVNRTYQE KDRRGGIFDA VFTRGDQSKL LTSRHDFKEK NLKEISDLIK  240
KELTEGKALG LSHTYANVRI NHVINLWGAD FDSNGNLKAI YVTDSDSNAS IGMKKYFVGV  300
NSAGKVAISA KEIKEDNIGA QVLGLFTLST GQDSW                             335

SEQ ID NO: 4           moltype = AA  length = 235
FEATURE                Location/Qualifiers
REGION                 1..235
                       note = Synthetic sequence
source                 1..235
                       mol_type = protein
                       organism = synthetic construct
SEQUENCE: 4
IVGGYTCAAN SIPYQVSLNS GSHFCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DSCQGDSGGP  180
VVCNGQLQGI VSWGYGCAQK NKPGVYTKVC NYVNWIQQTI AANLFLFLFL FLFLF       235

SEQ ID NO: 5           moltype = AA  length = 12
FEATURE                Location/Qualifiers
REGION                 1..12
                       note = Synthetic sequence
source                 1..12
                       mol_type = protein
                       organism = synthetic construct
SEQUENCE: 5
LFLFLFLFLF LF                                                      12

SEQ ID NO: 6           moltype = AA  length = 253
FEATURE                Location/Qualifiers
REGION                 1..253
                       note = Synthetic sequence
source                 1..253
                       mol_type = protein
                       organism = synthetic construct
SEQUENCE: 6
IVGGYTCAAN SIPYQVSLNS GSHFCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DSCQGDSGGP  180
VVCNGQLQGI VSWGYGCAQK NKPGVYTKVC NYVNWIQQTI AANQLGAGAF GGYQVNPYVG  240
FEMGYDWLGR MPY                                                     253
```

-continued

```
SEQ ID NO: 7            moltype = AA  length = 30
FEATURE                 Location/Qualifiers
REGION                  1..30
                        note = Synthetic sequence
source                  1..30
                        mol_type = protein
                        organism = synthetic construct
SEQUENCE: 7
QLGAGAFGGY QVNPYVGFEM GYDWLGRMPY                              30

SEQ ID NO: 8            moltype = AA  length = 224
FEATURE                 Location/Qualifiers
REGION                  1..224
                        note = Synthetic sequence
source                  1..224
                        mol_type = protein
                        organism = synthetic construct
SEQUENCE: 8
IVGGYTCAAN SIPYQVSLNS GSHFCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DSCQGDSGGP  180
VVCNGQLQGI VSWGYGCAQK NKPGVYTKVC NYVNWIQQTI AANC                  224
```